US008432543B2

(12) United States Patent
Frankel

(10) Patent No.: US 8,432,543 B2
(45) Date of Patent: Apr. 30, 2013

(54) METHOD AND SYSTEM FOR RAMAN, FLUORESCENCE, LITHOGRAPHIC, STIMULATED EMISSION AND PHOTOCHEMICAL IMAGING BEYOND THE DIFFRACTION LIMIT

(76) Inventor: Robert D Frankel, Rochester, NY (US)

(\*) Notice: Subject to any disclaimer, the term of this patent is extended or adjusted under 35 U.S.C. 154(b) by 44 days.

(21) Appl. No.: 13/236,994

(22) Filed: Sep. 20, 2011

(65) Prior Publication Data
US 2012/0069332 A1 Mar. 22, 2012

Related U.S. Application Data

(60) Provisional application No. 61/384,558, filed on Sep. 20, 2010.

(51) Int. Cl.
*G01J 3/44* (2006.01)
(52) U.S. Cl.
USPC .......................................................... 356/301
(58) Field of Classification Search ........... 356/300–334
See application file for complete search history.

(56) References Cited

U.S. PATENT DOCUMENTS 5,034,613 A \* 7/1991 Denk et al. ................. 250/458.1

\* cited by examiner

*Primary Examiner* — Tara S Pajoohi Gomez
(74) *Attorney, Agent, or Firm* — Henry M. Feiereisen LLC

(57) ABSTRACT

Systems and methods for hyper-resolution beyond the diffraction limit of optical microscopes for applications in spectroscopy, absorption and lithographic photochemical patterning are described. These systems are based on interference of a pump pulse and a Stokes laser pulse which interfere to localize the population of an excited vibrational state in an area that is smaller than the scanning resolution of the microscope. Another (interfering) Stokes pulse has an annular shape at focus and destructively interferes with the the Stokes laser pulse. This destructive interference causes narrowing of the population distribution of the vibrational excited state well below the diffraction limit, which in turn localizes the population of the central electronic excited state by a separate actinic laser pulse having a lower energy than the ground state excitation energy of the molecule.

A stepped photolithography system uses two photomasks to produce photoresist images capable of printing features smaller than 10 nm.

19 Claims, 10 Drawing Sheets

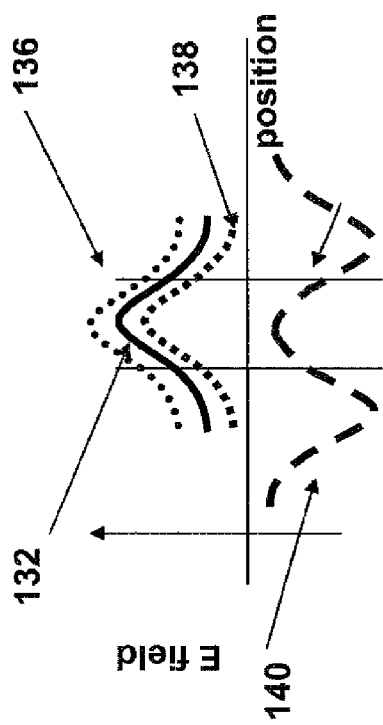
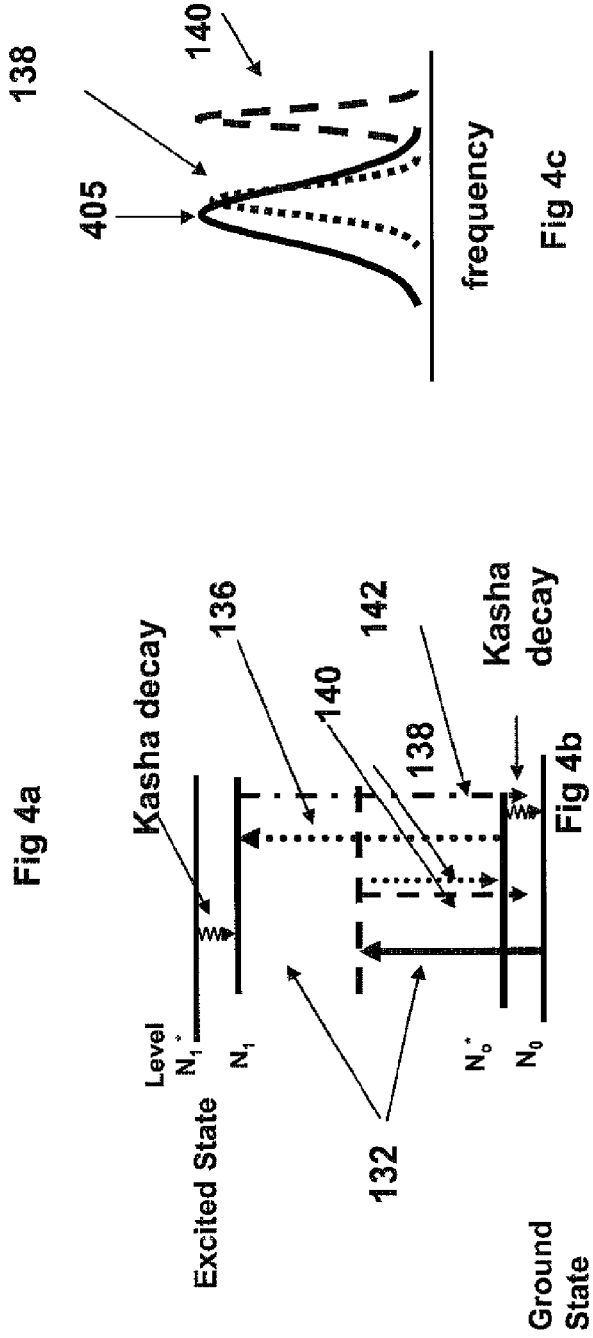
Figure 4

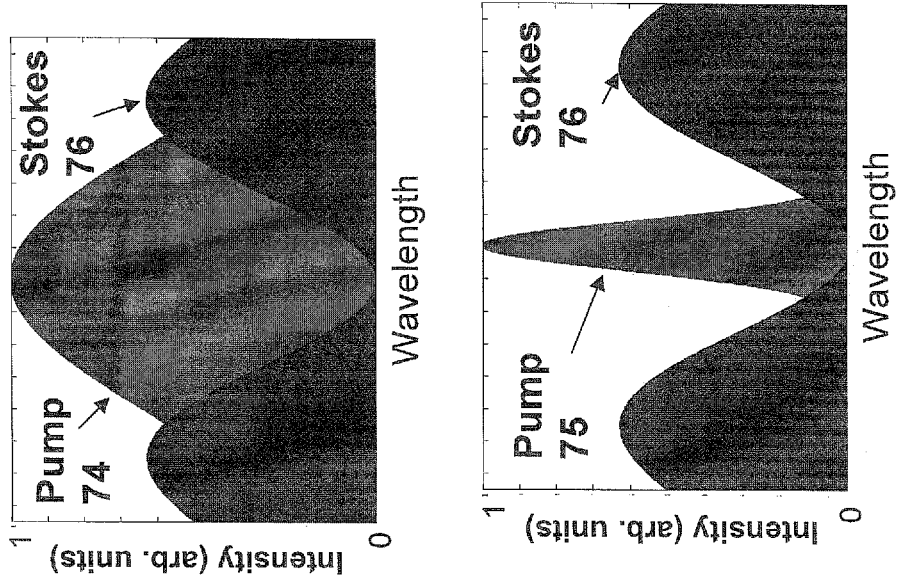
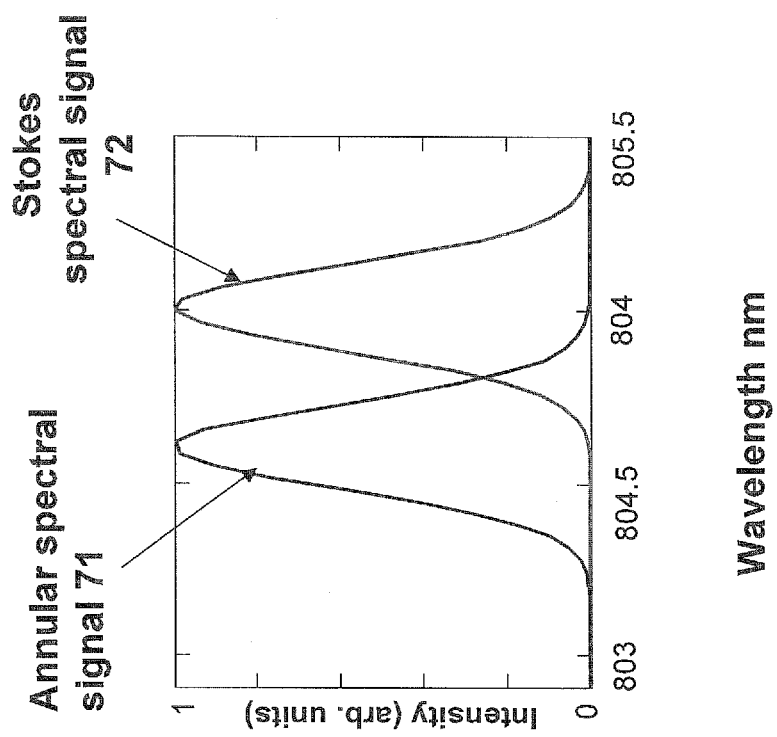
FIG 7a
FIG 7b

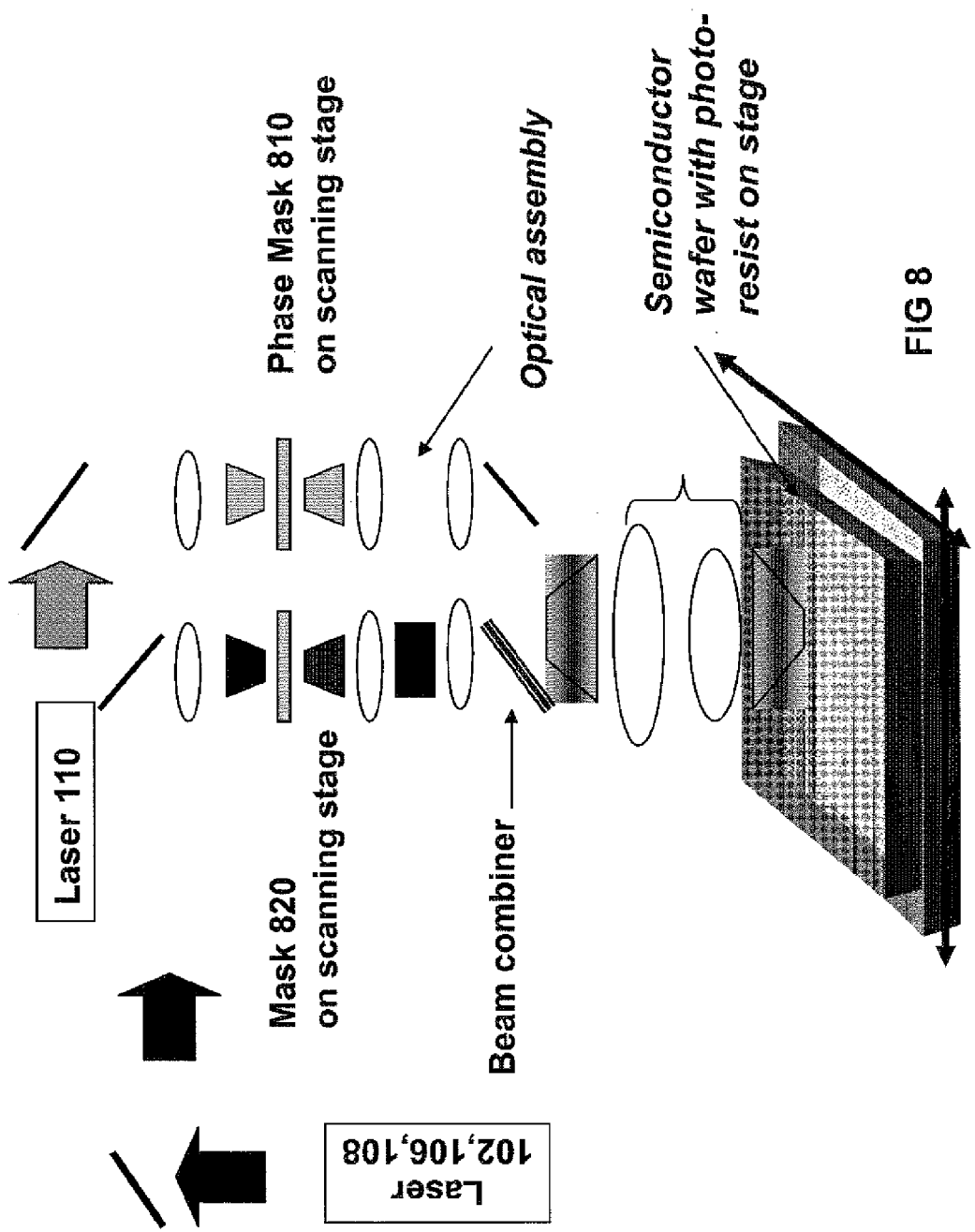

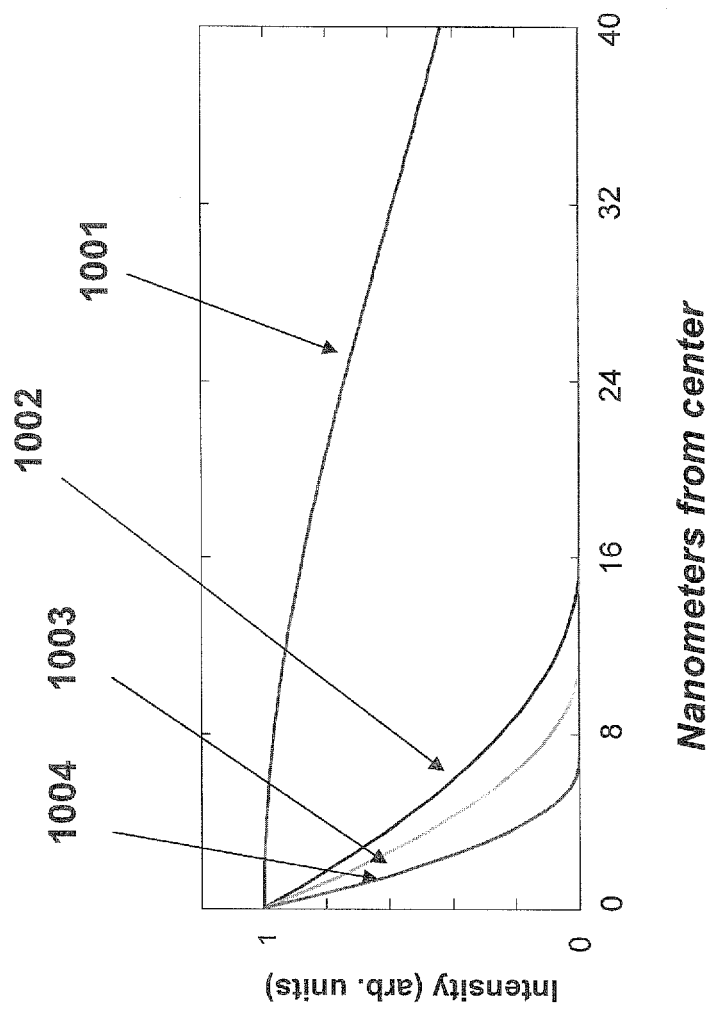

METHOD AND SYSTEM FOR RAMAN, FLUORESCENCE, LITHOGRAPHIC, STIMULATED EMISSION AND PHOTOCHEMICAL IMAGING BEYOND THE DIFFRACTION LIMIT

CROSS-REFERENCE TO RELATED APPLICATIONS

This application claims the benefit of prior filed U.S. provisional Application No. 61/384,558, filed Sep. 20, 2010, the entire content of which is incorporated herein by reference.

FIELD OF INVENTION

This invention relates to the field of Coherent Anti-Stokes Raman Scattering (CARS), fluorescence, absorption, stimulated fluorescence, stimulated Raman and lithographic photochemical patterning microscopy, and more particularly to the field of non-linear two to four-wave coherent and incoherently mixed optical imaging in the presence of specific molecular bonds that are to identify and image molecules, or to induce patterned photochemistry in the molecules with a resolution beyond the diffraction limit of the microscopic imaging system being used.

BACKGROUND TO THE INVENTION

The following discussion of related art is provided to assist the reader in understanding the advantages of the invention, and is not to be construed as an admission that this related art is prior art to this invention.

The resolution limit in traditional optical microscopy is limited by the numerical aperture of the microscope (NA) and the wavelength $\lambda$ of imaging light, generally referred to as Raleigh limit or diffraction limit; and is equal to $0.61(NA)\lambda$. This limit has recently been overcome in the case of fluorescence microscopy with Stimulated Emission Depletion (STED) microscopy by applying the statistical localization techniques of PhotoActivation Localization Microscopy (PALM) and STochastic Optical Reconstruction Microscopy (STORM). These techniques are based on the physics of incoherently driven optical fluorescent transitions in dyes or other fluorescent molecules. In these techniques, light of one color turns off a fluorescent molecule, while light of another color is used to photo-stimulate the release of fluorescent photons producing an image of the molecules.

In STED microscopy, a first focused circular pulsed laser beam is used to provide an excited electronic state in fluorescent molecules at the focus of a microscope objective. Then a second pulsed laser beam of a different wavelength, focused to an annular shape is used to cause stimulated emission from the excited molecules in the annular spot for de-exciting the molecules back to the ground state manifold of the molecule. The annular beam is about the same size as the first beam but with a zero in the electric field at the center of the annulus of the stimulating beam. Unfortunately, this technique depends on the presence of efficient fluorescent molecules, where the fluorescence is often provided by a label rather than the intrinsic molecules. However, this technique is unable to identify intrinsic molecules that are not strongly fluorescent.

PALM and STORM work by turning fluorescent emission from isolated dye molecules off and on and finding the center position of the emission peak of individual fluorescent molecules. These two techniques work best with a low concentration of fluorescent molecules.

Since not all molecules are strongly fluorescent, Raman microscopy is used to measure the vibration levels of intrinsic molecules in biological tissue, solid phase materials or on surfaces. In a Raman scattering process, a laser photon of a defined and stable wavelength is scattered from a molecule and shifted in wavelength by the vibrational energy level of a particular molecular bond. Raman spectroscopy and Raman microscopy typically operates with incident (excitation) light in the ultraviolet, visible or near infrared spectral regions which are weakly absorbed in many solvents such as water.

Conventional Raman microscopy has several drawbacks that have limited its application in biological imaging and hyper-resolution imaging, with hyper-resolution imaging defined as imaging with a resolution exceeding the diffraction limit. These include the following: 1) The incident laser light can stimulate fluorescent emission in the molecules under study, the solvent, or tissue under study which can coincide with the Stokes shifted Raman spectrum. 2) In general, the Raman process is inefficient. The collection efficiency of Raman scattered photons may be approximately $10^{-12}$. Since high intensity radiation of samples is limited by laser heating, Raman imaging and spectroscopy is a very slow process. 3) The scattering is non-directional, requiring very short working distances or very high numerical aperture lenses and microscope objectives. 4) Spectra of complex organic molecules may overlap, making it difficult to discriminate between different types of molecules. 5) Resolution is limited to that of the microscope which in general may be 0.4 microns or larger. 6) In small focal spots there are fewer molecules to produce the weak Raman scattering signal. 7) Poor scattering efficiency coupled with poor discrimination of signal and background makes detection of low concentrations of molecules impossible. 8) Raman transitions have very short excited state lifetimes. Virtual states for non-resonant Raman have femtosecond lifetimes, while Resonant Raman transitions have lifetimes in the 100 femtosecond range. These fast excited state decays make it impossible to use STED imaging techniques to achieve hyper-resolution imaging.

Variations of Raman imaging exist that can overcome several, but not all, of these deficiencies. For example, a longer excitation wavelength can be used to reduce background fluorescence; however, the molecular scattering cross section decreases with the inverse fourth power of the incident wavelength and the resolution in the image decreases with longer wavelength imaging. Alternatively, using resonant Raman spectroscopy can increase the Raman scattering cross section to $10^{-4}$ efficiency, albeit at the expense of significant enhanced fluorescent emission, and in tissues this is limited by the very strong background absorption in the ultraviolet (UV). The use of short laser pulses and time-gating the spectral acquisition to the sub-nanosecond regime may alleviate the adverse effects caused by fluorescence emission. However, most molecules have resonant absorption in the UV region which limits the use in plastic containers or the ability to see below the surface of biological tissues. Furthermore UV light often causes significant damage to biological and plastic materials, limiting its use to thin or surface samples.

A Raman technique that overcomes many of the aforementioned deficiencies is referred to as Coherent Anti-Stokes Raman Spectroscopy (CARS). CARS is a four-wave mixing process involving the generation of coherent vibration in the probed medium. Disadvantageously, the traditional CARS process produces a non-resonant incoherent background which can mask the measurement signal. This background is often caused by transitions involving solvent virtual levels. In addition, because the laser photons have to be tuned to the molecular transitions of interest, two or more different tunable picosecond lasers may be required. CARS also lacks adequate sensitivity, has a resolution limited to at most 300-400 nm, and cannot distinguish overlapping Raman bands.

Recently, Stimulated Raman Scattering (SRS) microscopy has demonstrated enhanced sensitivity over classical Raman microscopy, and similar stimulated emission techniques have been shown to enhance the sensitivity of imaging with poorly fluorescent materials. These techniques rely on Stimulated emission of a traveling wave field to enhance the emission of light into the forward propagating laser field. This is the same process that produces "gain" in a laser beam propagating in a laser amplifier. However the femtosecond to picosecond lifetime of the excited states of these molecules have limited the application of STED techniques for use with these techniques for hyper-resolution imaging.

The published US patent application 2010/0238438, incorporated herein by reference in its entirety, describes systems and methods for probing a Raman signature of a sample with a resolution exceeding the diffraction limit. These systems, called GASSE (Gain Saturated Stimulated Emission) and iGASSE (inteferometric GASSE), detect a stimulated Raman (or stimulated fluorescence) signal produced in a sample located at the focal spot of microscope. A Gaussian pump pulse produces a population inversion in a real or virtual level. Two additional pulsed laser beams (Stokes beams), of which a central Stokes beam has a Gaussian beam profile and another Stokes beam has an annular beam profile, are also focused to the focal spot. The two pulses are very close together in energy and compete to produce gain in each pulse. The annular Stokes pulse has higher intensity than the Gaussian pulse. Two mechanisms for gain competition enable hyper-resolution, gain saturation and suppression of polarization through interference. In gain saturation, the annular pulse drives the molecules into gain saturation or close to a 50:50 distribution of energy in the ground and excited state. This reduces region of central gain to produce narrowed emission. Alternatively, the annular pulse is designed to be 180° out of phase of the central pulse and thus destructive interference reduces the gain over most of the temporal width of Stokes pulses which causes emission from the central Stokes beam to narrow well below the diffraction limit. A two-dimensional image of the sample is produced by scanning the combined beams across the sample. Since the wavelengths of the Stokes pulses are different, they cannot interfere over their entire pulse lengths. This problem is solved by making the pump pulse shorter than the Stokes pulses. The system may find applications in biomedical and semiconductor technology. GASSE can provide an optical technique having an imaging resolution of better than 40 nm, for example, about 5-40 nm, with a high sensitivity and concurrent spectroscopic analysis. It can image deeply below the surface which is not possible with resonance Raman techniques operating in the UV.

However, there are hyper-resolutions imaging situations which cannot be solved with GASSE imaging. GASSE techniques populate excited states in both the center and surround of the focal spot. The photochemical activity in the surround is not depleted. Therefore time delayed photochemical or emission processes can take place over the entire focal spot. In addition GASSE does not provide hyper resolution in absorption microscopy, or on stimulated CARS imaging or resonant CARS imaging.

It would therefore be desirable and advantageous to address this problem and to obviate other prior art shortcomings by providing a hyper-resolution imaging technique that can be used to pattern photochemical active molecules, such as in photoresist used to pattern microchips, photoactivation in biological tissues, or fluorescent molecules that dose not require gain saturation in a medium. It would also be desirable to provide hyper-resolution patterning in CARS microscopy, and to improve the signal-to-noise ratio in CARS-, Raman- and resonance Raman-imaging so as to approach the sensitivity of fluorescence imaging.

SUMMARY OF THE INVENTION

The systems and methods described herein make use of four and optionally five laser beams. Two laser beams, referred to as pump beam and Stokes beam, are used for vibrational level excitation in a target molecule, creating a transient change in the absorption profile of the target molecule by populating a vibrational excited state. Another beam, referred to as interfering or annulus beam, is used to narrow the vibrational excited state spatial distribution enabling imaging resolution beyond the diffraction limit of a microscope by interfering with the Stokes beam. The fourth laser beam, referred to as actinic beam, provides the population of the electronic excited state that either creates fluorescence (enhancing the molecular Raman signal, either with or without the use of the interfering beam), initiates a hyper-resolution photochemical event pattern or produces hyper-resolution CARS imaging in a scanning microscope. The actinic beam may also provide the contrast in absorption microscopy. In some embodiments, as described below, a fifth laser beam referred to as the Stimulated Emission (SE) laser beam may be added to the system to produce stimulated emission from the excited state of the fluorescent molecule.

According to one feature of the present invention, a vibrational excited state is created by two laser beams that are focused to a spot by a microscope or focused to a pattern defined by a photomask and imaged to the microscope focal plane. The pump laser beam has a picosecond or sub-picosecond pulse width and creates a virtual or real excited state. A SE laser beam with a picosecond or sub-picosecond pulse width may be used to produce stimulated emission from the excited virtual state into a vibrational excited state in the ground state manifold of a target molecule.

According to another feature of the present invention, the added energy of two photons from the pump laser beam may be selected so that their sum is less than the resonant excitation energy of the target molecule. These photons may have a wavelength between 380 nm and 1000 nm depending on the energy of the electronic transition. This minimizes parasitic two-photon absorption effects. In an alternative choice of the two-photon summed energy of beam, the energy of one beam is greater than the first excited state manifold of the target molecule, but less than the lowest excited state of the second excited state manifold of the molecule. These photons may have a wavelength between 250 nm and 500 nm depending on the energy of the electronic transition. However, the added energy of the two beams should also be less than the energy of the second excited state.

According to another feature of the present invention, the actinic laser beam has picosecond or sub-picosecond pulse width, causing a transition from the vibrational excited state to a real or virtual electronic state of the molecule by a one-photon process or a multi-photon process. In a one-photon process, the wavelength of the actinic beam may be between 220 nm and 650 nm depending on the energy of the electronic transition and the energy levels excited by the pump and stokes photons. The actinic laser beam is also focused by a microscope to a spot, or to a reduced image pattern of a photomask. The photon energy of the actinic laser beam is less than the equilibrium absorption edge of the molecule, or is outside the ground state electronic resonant absorption band of the molecule. However, the photon energy of the actinic laser is transient within the absorption bandwidth of the molecule when the molecule has a vibrational band that has an excited state populated by the actions of the two laser beams. If the excited state is real and the molecule is fluorescent, then the molecule may emit a fluorescent photon that encodes the vibrational excited energy state of the molecule. This process will be referred to as Fluorescent Encoded Anti-Stokes Raman Emission (FEARE) spectroscopy. The molecule may also initiate a photochemical process. In this case, the process will be referred to as Photochemical Encoded Anti-Stokes Raman Chemistry (PEARC). If the excited electronic transition is a virtual level, the standard CARS spectrographic process is recovered.

According to another feature of the present invention, the fourth actinic laser beam may have a polarization that is orthogonal to that of the pump beam and the Stokes laser beam and may be delayed relative to the laser pulses from the lasers other than the actinic laser. Resolution-spoiling multiphoton effects are minimized with orthogonal polarization. The actinic laser beam may be used for two- or three-photon excitation of fluorescence or photochemistry.

According to another feature of the present invention, the interfering (annulus) laser beam has picosecond or sub-picosecond pulse width. This laser has a wavelength close to that of the Stokes laser. The wavelength peak of the interfering pulse may be shifted by 5-20 wavenumbers from the Stokes pulse. This interfering Stokes laser beam is 180° out of phase with the Stokes laser beam at its temporal pulse center peak. The wavelength difference between the central wavelength of the interfering laser beam and the pump laser is non-resonant with the energy bandwidth of the vibrational transition populated by the difference of wavelength of the pump beam and the Stokes laser beams. The actinic laser beam may be focused to an annulus, or sinusoidal intensity pattern, or through a separate imaging mask to a circular pattern. The actinic laser interferes with the Stokes laser beam to create a spatially narrowed distribution of vibrational excited states that contribute to hyper-resolution fluorescence, photochemistry, or CARS imaging. The interfering laser beam may have the same pulse width, a longer pulse width, or correspondingly a narrower bandwidth than the Stokes beam. The spatial localization of the size of the fluorescent, photochemical or CARS region may be less than 40 nm and as small as a few nanometers.

According to another feature of the present invention, multiple vibrational energies may be encoded in a single fluorescent signal. In this embodiment, the Stokes laser produces a broad-band femtosecond pulse that creates populated vibrational states of the target molecules at the focus of the microscope that may be used to create a series of spectrally encoded regions that may be decoded by Hadamard transform spectroscopy The actinic laser is also a broadband laser where the wavelength range is separated into spectral regions by a dispersive device, for example by a grating, and is then intensity-, phase- or polarization-modulated by a liquid crystal array, whereafter the different wavelengths are recombined by a grating and focused to create a multiplicity of actinic wavelengths that cause a multiplicity of vibrational states to populate the same fluorescent electronic excitation band. The wavelength distribution of the liquid crystal modulator is then modified by a Hadamard transform basis function, and multiple fluorescent signals are added to produce a series of signals that can be used to reconstruct the Raman spectrum of the sample.

According to another feature of the present invention, a fifth laser beam, called the Stimulated Emission (SE) laser beam, may be added to the system to produce stimulated emission from the excited state of the fluorescent molecule. The SE laser enables signal enhancement from fluorescent states with very low quantum efficiency. Addition of the SE photon creates stimulated emission FEARE, referred to as sFEARE. Furthermore, the entire class of techniques disclosed in this invention may be referred to as Stokes Interference State Controlled (SISC) imaging.

According to another aspect of the present invention, a microscope system may be constructed with two patterned photomask images that may be scanned and superimposed at the focus of a microscope focal plane. One photomask, is exposed using the pump laser beam, the Gaussian Stokes laser beam and the actinic laser beam in combination. The other photomask, embodies as a phase mask, is exposed using the actinic laser beam. The features of a phase mask are known in the art. These masks are used for multiple micro-stepped exposures (each step is a fraction of the maximum image pitch of the microscope) on the same photoresist laser to create a hyper-resolution pitch image with hyper-resolution features. The beams may be scanned over the mask with the stage moving to produce a large image hyper-resolution image field in a photoactive material, such as photoresist.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIG. 4 shows an intensity distribution (a); an energy level diagram of the three laser pulses (b); and an energy difference of the Stokes pulses in the homogenous transition bandwidth of the emission transition (c);

FIG. 7 shows the spectra of a Gaussian and Annular Stokes pulse (a) intensity and beat intensity of two interfering 2 picosecond Stokes pulses and 2 and 0.35 picosecond pump pulses (b);

FIG. 8 shows a photoresist exposure system with two photomasks;

FIG. 10 shows Point-Spread-Functions of FEARE/PARC systems with increasing intensity in the interfering annular PARC beam.

DETAILED DESCRIPTION OF EXEMPLARY EMBODIMENTS

Figure 1:
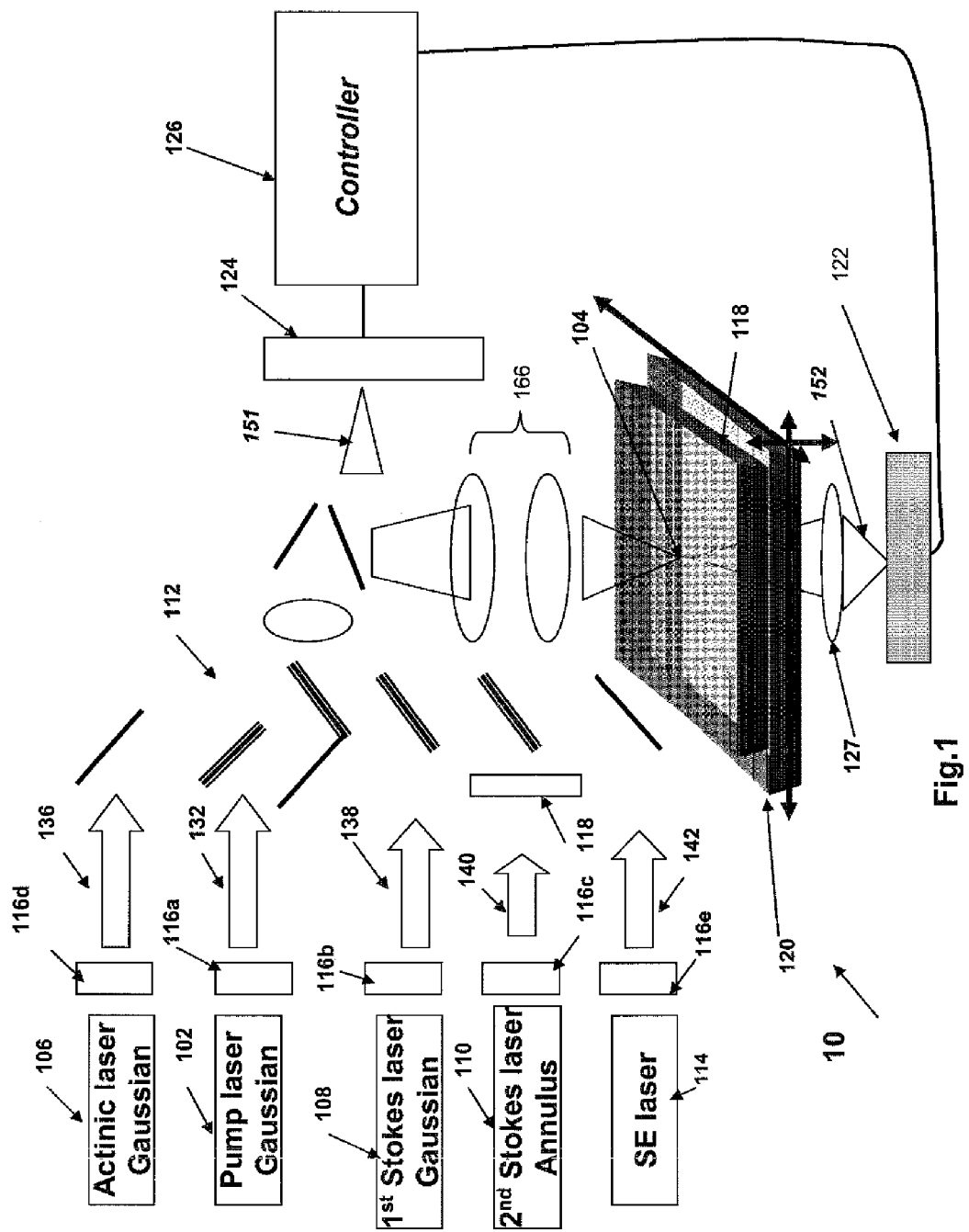
FIG. 1 shows schematically a system for scanning FEARE or PEARC microscope according to the invention.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Referring now to FIG. 1, a laser system 10 includes four lasers 102, 106, 108 and 110, as well as an additional (optional) laser 114. The laser 102 is referred to as pump laser emitting laser pulses of picosecond duration with a Gaussian beam profile in form of a pump beam 132. The pump beam 132 is focused in a diffraction limited spot 104 in the focal plane of a high numerical aperture (NA) microscope objective 166. A target sample 114 to be investigated is located in or near the focal plane. A pulse from pump beam 132 will also be referred to as pump pulse 132.

FIG. 1 also shows conventional phase modulators 116a, 116b, 116c, 116d, 116e, such as liquid crystals and solid state modulators, disposed in each laser beam 132, 136, 138, 140 and 142. The phase modulator 116d may also be used to alter the polarization of laser beam 136 to make it orthogonal to the other laser beams. The operation of the phase modulators 116a, 116b, 116c, 116d, 116e will be described in more detail below.

The laser 108 may be referred to as a first Stokes laser 108, also emitting laser pulses of picosecond duration with a Gaussian beam profile in form of a pump beam 138. The pump beam 132 is used to pump the virtual level that will interact with pulsed laser beam 138 by two wave mixing (or viewed another way be stimulated emission) to populated the excited vibrational level of the target molecule. The wavelength of the picosecond laser pulses in pump beam 138 from the first Stokes laser 108 is Stokes-shifted from the wavelength of the pump laser 102 by the energy of the populated energy level of the excited vibrational states of the target sample and is also focused at the diffraction limited spot 104. The pump beam 138 will also be referred to for short as "Stokes" laser beam, and a pulse from pump beam 138 as "Stokes" pulse 138 which is used to cause the emission from the virtual state stimulated by pump beam 132 in order to populate the vibrational excited states of the target sample. The energy difference between a pump pulse 132 and a Stokes pulse 138 is within the vibrational energy bandwidth of a bond in the target sample molecule.

The laser 110 may be referred to as a second Stokes laser or interfering laser 110, emitting a pulsed picosecond laser beam 140 which is focused to an annulus in the focal plane of the microscope objective 166. The laser beam 140 will also be referred to as "interfering" laser beam 140, and a pulse from the laser beam 140 as "interfering" pulse 140. The annulus in the focal plane is created by a phase shifting plate 118. Alternatively, a sinusoidal illumination may be produced by splitting the surround stokes beam in two beams and creating high NA off-axis interferometric illumination, as used in structured illumination microscopic systems or interferometric lithography imaging systems.

Figure 5:
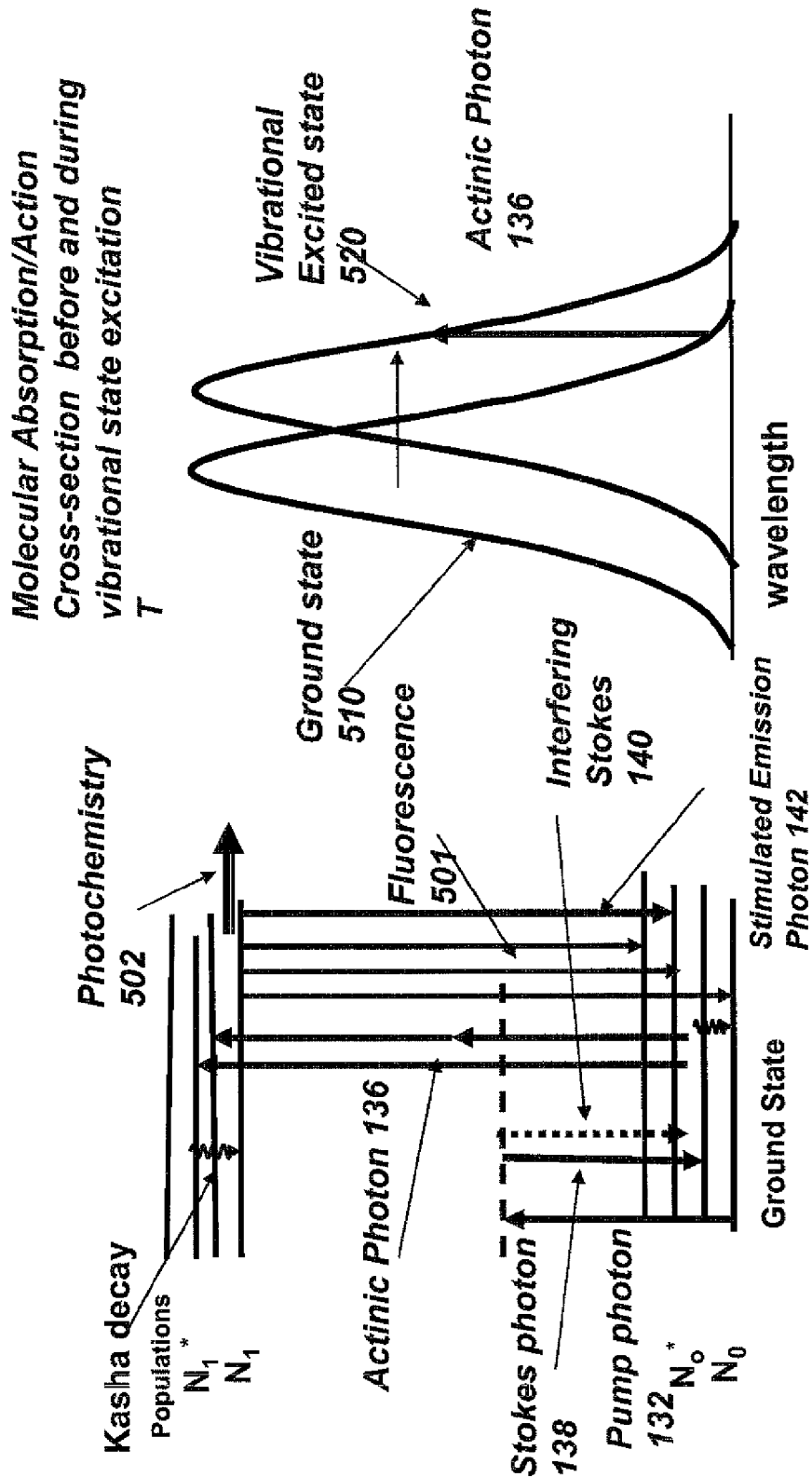
FIG. 5 shows the energy diagram of a target molecule (a) and the alteration of the absorption profile by transient excitation by photons from the Gaussian pump laser and Stokes laser beams (b)

The laser 106 is referred to as actinic laser 106, emitting a pulsed picosecond Gaussian laser beam 136 which is focused in the focal plane of the microscope objective 166. Laser beam 136 will also be referred to as "actinic" laser beam 136, while a pulse from the laser beam 136 will be referred to as "actinic" pulse 136. Population of the vibrational excited level that will alter the absorption profile at the target wavelength is shown in FIG. 5 for the actinic pulse 136. Vibrational energy can be transferred from the vibrational bond to the valence electrons that participate in the excited state transition by adding energy to actinic laser pulse 136 on a femtosecond time scale. The photon energy of the interfering pulses 140 is close to that of the Stokes pulses 138, with the energy difference between pump pulses 132 and interfering pulses 140 being just off-resonance with respect to the vibrational transition of the target molecule. The wavelength difference between the two pulses may be 5-20 nm. The Stokes pulses 138 and interfering pulses 140 are emitted so as to arrive at the focal spot 104 simultaneously with the pump pulses 132.

The actinic laser may also be a broadband laser where the wavelength range is separated into spectral regions by a dispersive device, for example by a conventional grating, and then intensity-, phase- or polarization-modulated by a liquid crystal array. The different wavelengths are then recombined by a grating and focused to create a multiplicity of actinic wavelengths. The optical components providing the separation, modulation and recombination may be incorporated in phase modulator 116d or added as a separate assembly, and are not illustrated in detail so as not to obscure the clarity of the drawing.

An example of the wavelengths of the 4 lasers that might be used in a FEARE system can be illustrated by looking at the organic molecule—methyl salicylate. Methyl salicylate has many uses. For example, the tobacco (*Nicotiana tabacum*) cultivar Xanthi-nc (genotype NN) produces high levels of salicylic acid (SA) after inoculation with the tobacco mosaic virus (TMV). Gaseous methyl salicylate (MeSA), a major volatile produced in TMV-inoculated tobacco plants, was recently shown to be an airborne defense signal. Methyl salicylate has a strong absorption band centered at 305.3 nm. At about 345 nm the absorption is just at the edge of the absorption band. The fluorescence peak in methyl salicylate is located at about 370 nm. In addition, methyl salicylate has a strong vibrational resonance band from the C=O stretching frequency of 1680 $cm^{-1}$. In a typical FEARE experiment, a pump wavelength of 700 nm in conjunction with a Stokes wavelength of 915 nm may be selected to excite a transition to the v=2 level in the ground state vibrational manifold. The actinic wavelength must be outside the absorption band of methyl salicylate and is, in the present example, selected to be located at an actinic wavelength of 350 nm. The sum of the actinic photon energy and the v=2 level vibrational energy then creates a 313 nm photon with an exciting energy which is well within the absorption band of the methyl salicylate and will stimulate stimulated Raman and fluorescent emission. To achieve hyper-resolution imaging of methyl salicylate, the energy difference between the pump photon and interfering photon must be away from the absorption edge of the v=2 ground state vibrational level, in which case the interfering photon wavelength might be chosen to be 915.8 nm, which is equivalent to a shift of 10 $cm^{-1}$, which is outside the vibrational level absorption band having a half-width of 15 nm. The required photon energies between 700 nm and 920 nm are well within the bandwidth of tunable Ti:Sapphire lasers. The 350 nm wavelength may be generated by frequency-doubling a Ti:Sapphire pulse with a nonlinear crystal, such as KDP.

Although the laser pulses 132, 134, 136 and 140 may arrive simultaneously at the focal spot 104, a slight time delay of several tens of femtoseconds to a few picoseconds between the pulses 132, 134, 136 and 140 may be considered. Time delays enable minimization of unwanted multi-photon effects. In order to further minimize unwanted multi-photon effects, the pulse 136 may have a polarization perpendicular to the other laser beams. The actinic pulse stimulates the molecule to go into the chemically active state that is required for fluorescent emission or to initiate photochemistry. If fluorescent or resonance Raman emission or photochemical activation (such as photoresist exposure) is required, the actinic photon populates a real electronic excited state. If non-resonant CARS emission is required, the actinic photons populate a virtual state. While a single actinic photon may be used, it is sometimes desirable to use 2 or more actinic photons to excite the transition of interest. Multi-photon actinic excitation may be used to provide enhanced penetration in biological tissues. The delay may be introduced, for example, by placing an optical delay line with movable mirrors in the laser beam 136. The pump laser beam 132, the two Stokes laser beams 138, 140 and the actinic laser beam 136 are combined using conventional optics, such as reflective and dichroic mirrors, beam splitters and lenses, commonly referred to by the reference symbol 112.

The system 10 may include an additional fifth Stimulated Emission (SE) laser 114 emitting a pulsed (SE) laser beam 142 that is merged with the beam paths of the other lasers 102, 106, 108, 110 by the optics 112 by adding another (dichroic) mirror.

It will be understood that the shape of the laser beams (Gaussian, annular) refers to their shape in the focal plane or at the focal spot after propagation through an optical system.

The Stokes laser beam 138 and the interfering laser beam 140 have specific characteristic wave fronts that enable imaging beyond the diffraction limit. In the illustrated example, the interfering laser beam 140 has an annular intensity profile shape, for example, in the form of a torus of intensity with substantially zero in intensity at the center of the focal point of the pump beam in the focal plane. The inner surface of the torus may be mathematically described by a parabola of revolution around the center of the microscope focus. This beam shape is introduced into the focus by a π-phase shifting plate 118. In an alternative embodiment (not shown), the output of interfering laser beam 140 may be split in two beams which are then recombined at the focal spot 104 to produce a sine wave interference pattern enabling higher resolution in a one dimensional scan. The Stokes beam laser 138 has a Gaussian intensity profile and overlays the pump laser beam.

The SE laser beam 142 may be added to create stimulated emission from the electronic excited state (Stimulated Emission FEARE—sFEARE). A photon from this laser is shown in FIG. 4 and FIG. 5. Addition of the SE laser pulse 142 may significantly enhance the probability of fluorescent photon emission when the excited state lifetime is short, <10 picoseconds. This stimulated process differs from GASSE, in that the SE laser beam 142 does not require a laser to cause interference with the stimulating beam to produce hyperresolution. Disadvantageously, however, this technique requires five laser beams.

The system 10 can be used for virtual level resonance, one-photon and two-photon excitation or 3-photon excitation FEARE/PEARC applications. Resonance fluorescence or photoresist exposure applications may require quartz optics which is transparent into the deep UV (DUV), possibly down to 240-190 nm. The lasers should emit picosecond or sub-picosecond pulses. The lasers may be implemented as four separate lasers, or may be seeded from one or two broad bandwidth lasers and separate spectral regions of a single pulse used to define the smaller bandwidth separate pulses, and should be tunable to stimulate different Raman or fluorescent resonances. The laser may be a tunable Ti:Sapphire laser, or a fiber laser with a continuum-generating fiber attached allowing spectral selection. The Ti:Sapphire laser may be configured as a parametric amplifier to produce two of the laser frequencies required.

Figure 2:
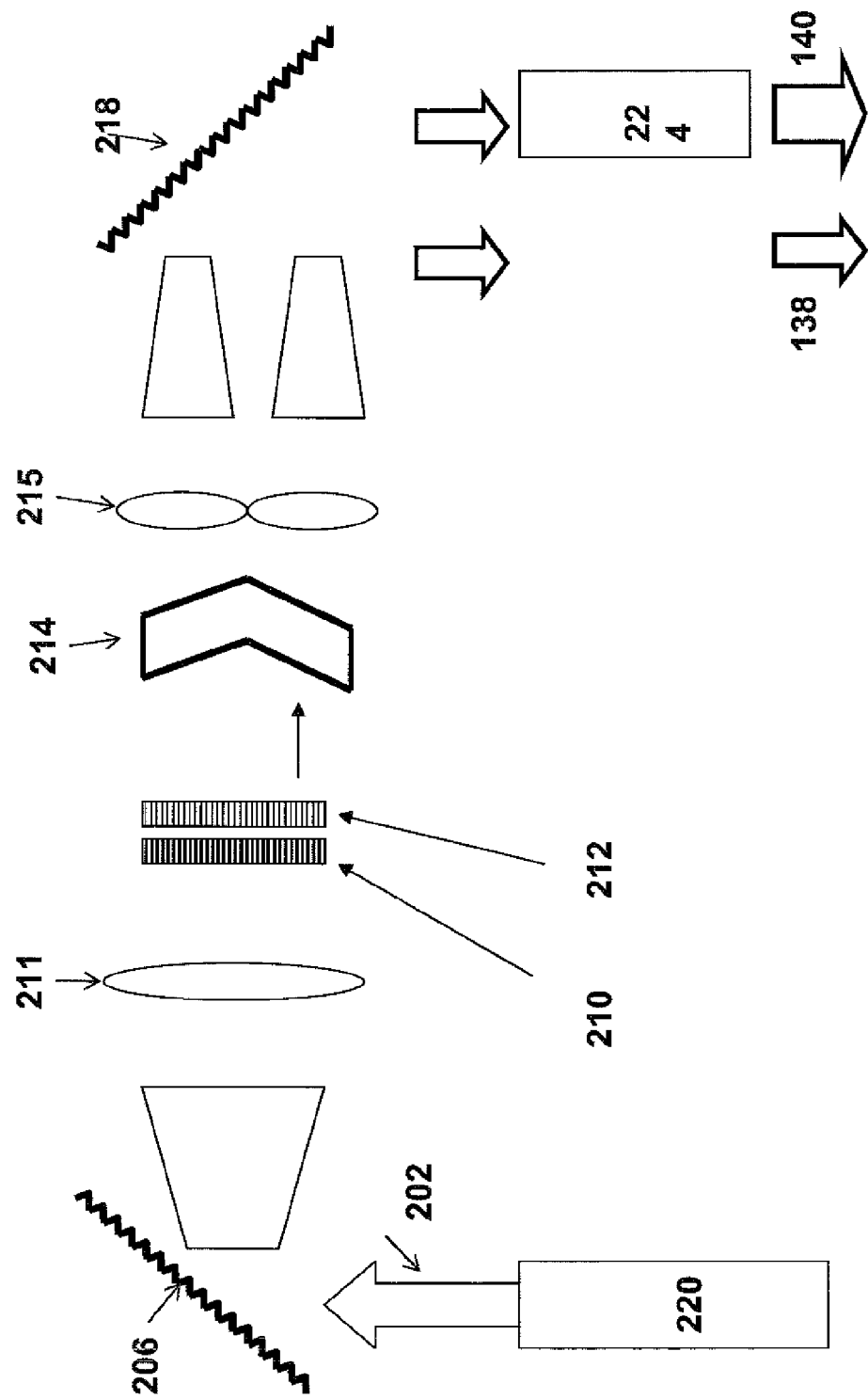
FIG. 2 shows a method of generating two Stokes pulses that are close together in wavelength and have a controlled phase and amplitude difference.

The Stokes laser beam 138 and the interfering laser beam 140 should have a controlled phase and amplitude relationship between each other, and should also be close together in wavelength, with their central wavelength preferably being separated by no more than the bandwidth of the vibrations excited levels, by 0.1-0.5 nanometers or less. FIG. 2 shows an exemplary method of generating the Stokes laser beam 138 and the interfering laser beam 140 from a single picosecond seed laser, such as a Ti: Sapphire solid state laser 220. The output beam 202 of laser 220 is spectrally dispersed by diffraction grating 206. The spectrally dispersed beam is collimated by lens 211. The phase of the frequency components of the beams may be changed by a first liquid crystal array 210 and the polarization may be altered by a second liquid crystal array 211. This is similar to an arrangement used in picosecond laser quantum phase control laser chemistry. The spectral components of each of the two Stokes pulses may then be spatially separated by tilted plates 214. The two beams are then refocused by lens 215 and the spectral components of each beam are then recombined by grating 218. Laser amplifier 224 may then amplify the resulting interfering laser beam 140 which should be 3-15 times more intense than Stokes laser beam 138. The laser beams 138 and 140 may then be frequency doubled or tripled as required for the application.

For UV resonance Raman and Fluorescence applications, frequency-doubled, frequency-tripled, or frequency-quadrupled solid state lasers may be required. The wavelength separation of the two Stokes lasers may be defined by the bandwidth of the bandwidth of the vibrational excited state.

The laser beams are combined by a beam splitter, overlapped in time and directed through a high NA microscope and focused on the sample. When the microscope is used to emit photons as in FEARE and CARS applications, back-reflected photon signal 151 and forward scattered photon signal 152 may be detected by a suitable spectrometer 122, 124 or filtered photo detector. The photons produced from annular and central stimulated emission should be separated. For some applications, the sample may be mounted on a scanning microscope stage 120. For some applications a scanning stage may not be required.

Figure 3:
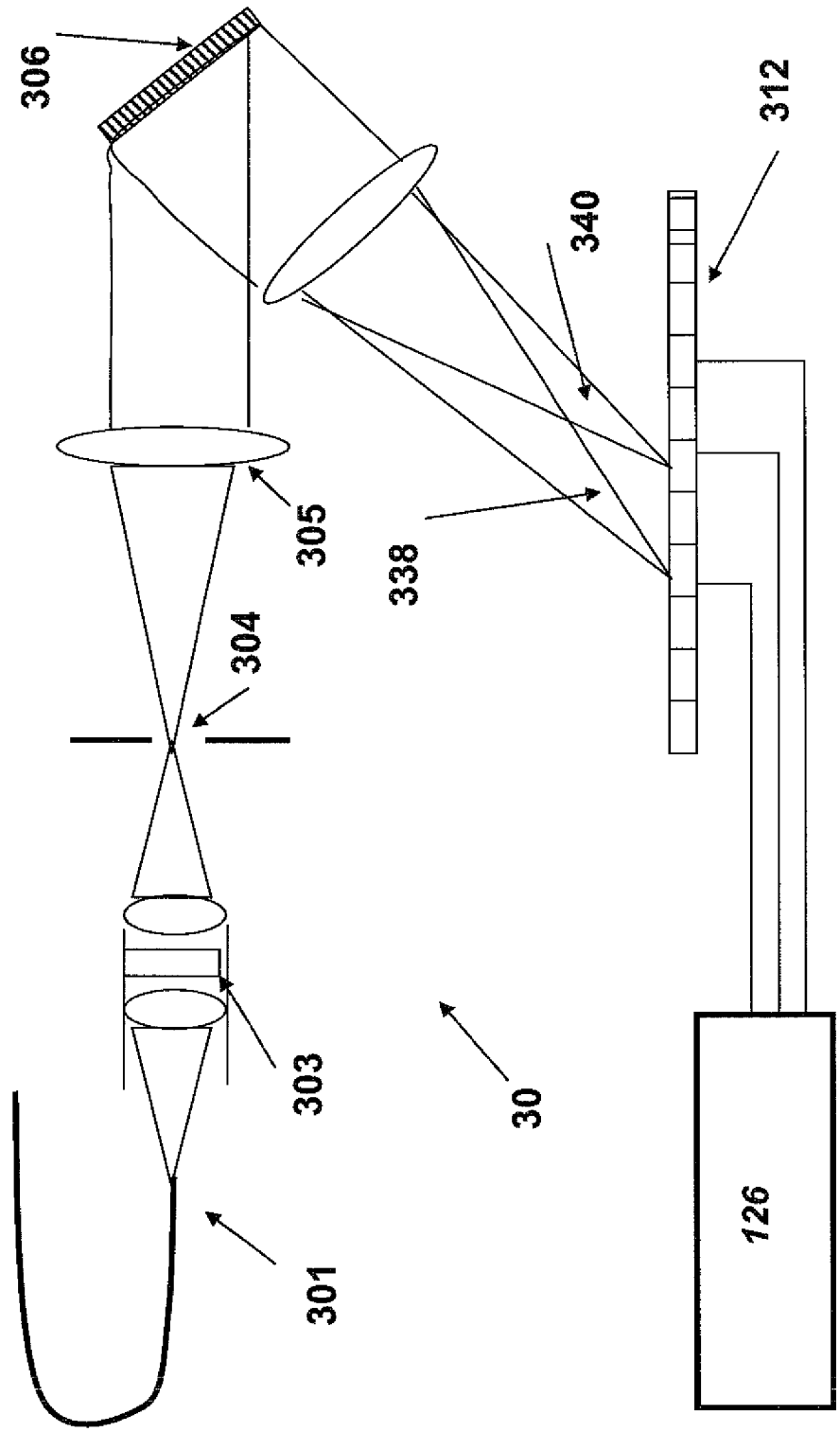
FIG. 3 shows a photon detection spectroscopy system used to collect signals with FEARE/CARS microscopy.

Spectrometers 122, 124 detect transmitted and backward scattered light from the sample 118 and may be implemented as a conventional grating spectrometer 30, as shown in more detail in FIG. 3. The grating spectrometer 30, in this example spectrometer 122 of FIG. 1, receives light through an optical fiber 301 from, for example, condenser 127 (see FIG. 1). The optical fiber 301 may be a multimode fiber or a single mode fiber. Multimode fibers have cores larger than 50 microns or more and hence will collect more light. Alternatively, free space optics may be used instead of an optical fiber. The backward scattered light may be detected by the "epi" light detection system 124, using a grating spectrometer 30 constructed in a similar manner as illustrated in FIG. 3. Epi scattering may be caused by multiple scattering beyond the focus of the laser, which may occur in thick samples, or by the small backscattered radiation component. The spectrometer may be positioned remote or integrated in the system 10. The light detection system of the spectrometer 30 may include silicon avalanche photodiodes 312, preferably fast photodiodes, or photomultiplier tubes. Stimulated emission photons are predominantly emitted in the forward direction of the stimulating beam laser modes. Gating the detector is typically used to eliminate background slower to appear fluorescence. The detection systems 122, 124 may be controlled by a controller 126.

FIG. 3 shows a signal collection optical fiber 301 that receives light from condenser 127. The output of the fiber is collimated and passes through pump optical filter 303 to remove the excitation pump light. This filter may be a multi-layer filter as used in Raman spectroscopy to remove excitation light. The light is then focused through the slit entrance 304 to a grating spectrometer, the grating 306 spectrally disperses and separates the stimulated emission enhanced central Stokes beam 338 and annular 340 Stokes beam. These beams are then focused by lens 304 on to an array of fast detectors 312. The controller 126 controls signal acquisition and compute the image. The signal for each image pixel is the photon signal from the Gaussian focus.

A diagrammatic representation of the FEARE/PEARC process and electric field distributions at the focal point 104 for the four laser beams 132, 136, 138, 140 are shown in FIG. 4a. The pump pulse 132 from pump laser 102 and the Stokes pulses 138 from laser 108 are focused to about the same diffraction limited focal spot diameter. Annular interfering laser pulse 140 is phase-shifted from pump pulse 132 by 180°. The pump pulse 132 has a higher optical frequency than the Stokes pulse 138 and thus will beat with the Stokes pulse 138 if they have identical polarization and overlap in time. The interfering pulse 140 from second Stokes laser 110 has an intensity distribution in the shape of an annulus produced by the π-phase change wave plate 118. As mentioned above, interfering laser beam 140 may in some cases be split by a beam splitter and recombined to interfere at the focal spot 104. In this case, the interfering pulse 140 may have a sinusoidal energy distribution in one direction. This geometry may enable higher resolution in the direction perpendicular to the sinusoidal fringes; however the resolution along the sinusoidal optical fringes is reduced. It may then become necessary to acquire the sample image from multiple directions to reconstruct the signal, as is done in computed tomography. Actinic pulse 136 is focused to a Gaussian spot. The actinic pulse may stimulate fluorescence or photochemistry. The actinic pulse 136 may be polarized to be orthogonal to the other laser pulses 132, 138, 140, and 142 so as to minimize unwanted nonlinear interactions.

FIG. 4c shows the difference between the Stokes pulse 138 and the pump pulse 132, as well as the difference between the interfering pulse 140 and the pump pulse 132 together with the vibrational transition in the frequency domain. The wavelengths of the Stokes pulse 138 and the interfering pulse 140 are generally selected to be close together and may be separated by one half the bandwidth of vibrational transition 405. For vibrational transitions of molecules in solution, this bandwidth may be 5-25 cm$^{-1}$. As indicated by the dashed lines in FIG. 4a, the two pulses 138, 140 may have a phase difference of 180° and destructively interfere with one another at their positions of overlap; other in-phase phase relations interfere constructively. This destructive interference can advantageously be used in FEARE/PEARC systems to increase the optical resolution beyond the diffraction limit, as will be discussed below. As shown in the energy level diagram of FIG. 4b, although the optical frequency of the Stokes pulse 138 and the interfering pulse 140 are close together, they can cause stimulated emission into the vibrational excited level in the ground state manifold of energy levels.

Energy level diagram in FIG. 5a represents potential target molecules in the FEARE/PEARC process. Photons 132 and 138 create a population inversion in the target molecule by populating ground state vibrational energy level $N_0^*$. This is a transient population inversion lasting 60-2000 femtoseconds, usually with an exponential decay in the inversion. The population inversion is achieved by stimulating excitation of a virtual level with pump photon 132 and stimulated emission from that level by photon 138. FIG. 5b shows the absorption band before vibrational excitation 510 and during population vibrational population inversion 520. As can been seen, actinic photon 136 is not absorbed by the ground state population absorption 510, but is strongly absorbed by the excited state distribution 520. FIG. 5a shows that absorption of actinic photon by the vibrational excited molecule can result in the initiation of a photochemical event 502 or the stimulation of fluorescence emission 501. The actinic photons may have energy suitable for 2 photon excitation if depth of penetration in a biological or semiconductor material is an issue. The result of the FEARE/PEARC process is hyper-resolution fluorescence or photochemistry. If the actinic photon is not energetic enough to initiate fluorescence, the result would be the normal CARS process with the added property of hyper-resolution.

Figure 6:
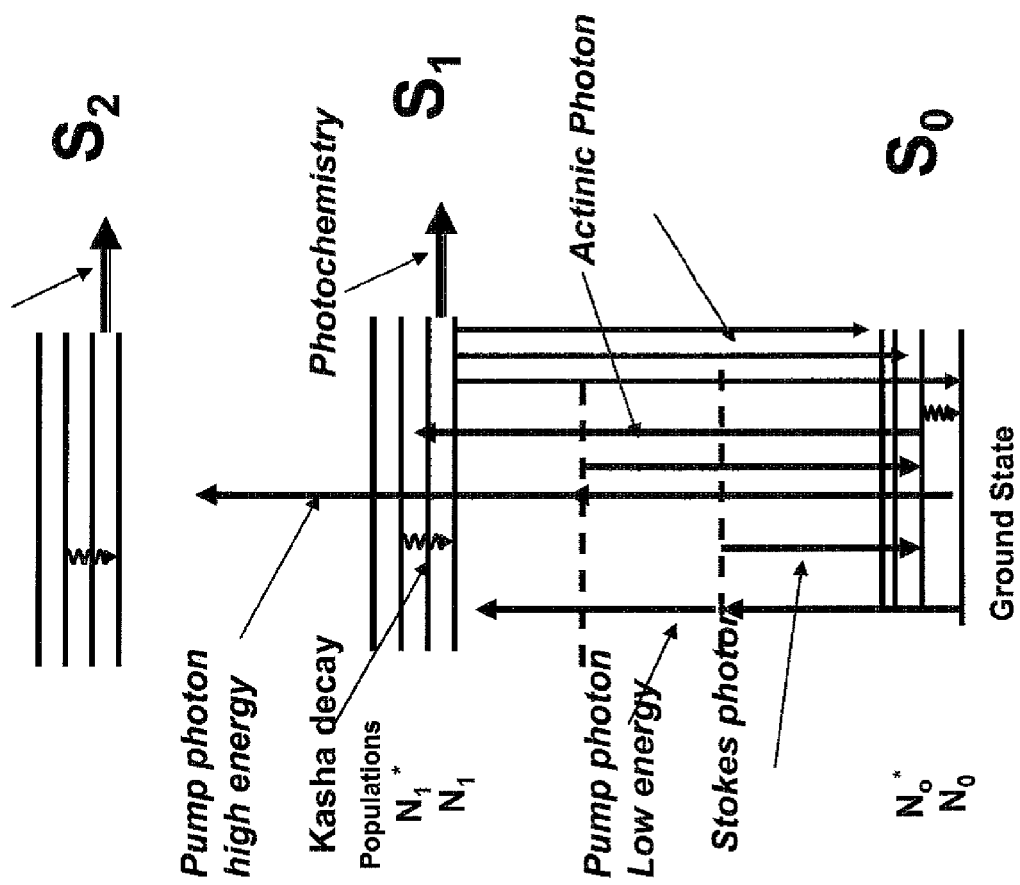
FIG. 6 shows wavelength choices for laser beam energies to reduce two-photon absorption effects.

The photon beams 132 and 138 must be intense enough to stimulate a significant population in the vibrational level without initiating a multi-photon process that stimulates the electronically excited state that is fluorescent or initiates photochemistry. A population inversion is not required. This can be minimized by choosing the energies of photons 132 and 138 to be less than one half of the lowest energy level in the excited state manifold $S_1$ of the target molecule, as shown in FIG. 6. Alternatively, the energies of photons 132 and 138 can be chosen such that the sum the energies of photons 132 and 138, or twice the energy of 132 and twice the energy of 138, are greater than the high-energy edge of the $S_1$ manifold and also less than the low-energy level of second excited state manifold $S_2$. This is also illustrated in FIG. 6. Further stimulus with actinic pulses 136 may be chosen to be polarized perpendicular to photons from laser beams 132, 138 and 140 to minimize its participation on multi-photon events.

The following discussion will provide an overview of the effect of the interference of the two Stokes pulses on the effectiveness of the actinic pulse in producing localized emission or photochemistry in three regions within the microscope focal spot—the center, the middle region where the intensity of both Stokes pulses are significant and the region of high annular intensity. Near the center, the annular Stokes pulse has close to zero intensity. Therefore, actinic photon absorption will occur in the vibrational excited level to initiate population of electronic excited state manifold $S_1$ which will initiate fluorescence, absorption, or photochemistry. Further out from the center of the Gaussian focus, the intensity of the annular interfering beam 140 increases and interferes with Stokes beam 138. The more intense interfering beam 140 is made, the closer to the center the beams can cancel each others electric field by interference. Complete interference will eliminate the population of vibrational excited level $N_0^*$. Still farther away from the center of the focal point 104, the optical field of the annular Stokes mode will dominate and no population of the electronic excited state manifold will occur because the energy difference between the pump beam 132 and the interfering laser beam 140 is not at resonance with the photon energy required to cause stimulate emission into the vibrational excited state.

It is therefore desirable to have spectrally separate Stokes pulses with a 180° phase shift for maximum resolution enhancement. Although it is difficult to spectrally separate and temporally phase-match the Stokes laser pulses 138 and the interfering laser pulses 140 over their entire pulse widths, phase-matching may be attained over a shorter pump pulse duration, as shown in FIGS. 7a-b. FIG. 7a shows the spectra 71, 72 of the interfering laser pulses 140 and the Stokes laser pulses 138, respectively, each having a duration (FWHM) of 2 picoseconds. The annular (interfering) Stokes pulse 71 has a spectral peak at 803.6 nm, while the Gaussian Stokes pulse 72 has a spectral peak at 804.0 nm. The spectral components of the two pulses 71, 72 are substantially separated, with a remaining small spectral overlap. Curve 76 in FIG. 7b shows the intensity of the beating Stokes pulses of FIG. 7a plotted as a function of time, with the phases being 180° out-of-phase at the temporal center of these pulses. The beat frequency plot is taken at the spatial position at the focal spot where the intensities of the annular and Gaussian Stokes pulses are equal. it is evident that the leading and trailing edges of the pulse move into phase, while interference is complete at the peak of the pulses. Effects caused by the leading and trailing edges can be minimized if the central pump pulse from pump beam 132 has a shorter duration than the pulses from Stokes beam 138 and interfering beam 140. Curve 75 in FIG. 7b shows the envelope of a 0.35 picosecond pump pulse, and curve 76 in FIG. 7b shows the envelope of a two picosecond pump pulse. As can be seen from FIG. 7b, a narrower central pump pulse can minimize the time when the emitters are in virtual excited state and the Stokes pulses are in phase. This strategy will work well for FEARE and PEARC, imaging where the pump and Stokes pulses would arrive at the focus simultaneously. The central Stokes pulse can also be made shorter than the annular Stokes pulse. This enables the bandwidth of the annular pulse to be reduced and moves the wavelength closer to the central Stokes bandwidth.

One application of Stokes Interference State Control (SISC) techniques will now be discussed with reference to DUV nanolithography. This discussion in based upon the absorption profiles of a HfO photoresist designed for exposure at 193 nm and having a low energy absorption edge that extends out 20 nm from maximum absorption at 193 nm. The hyper-resolution exposure system is assumed to use an actinic wavelength of 213 nm, which is outside the resist absorption band. As an example, the vibrational level of interest excited to produce absorption of the actinic photon may have a first excited ground state vibrational level of 1500 cm$^{-1}$. If an electron is placed in the first excited state by the pump and Stokes beams, the wavelength shift in transient absorption is about 6.1 nm. This added energy to an actinic photon is inadequate to create efficient absorption characteristic of the photoresist to enable high contrast exposures. Given the resist absorption profile it is desirable to shift the absorption edge by >18 nm to enhance the resist absorption by several hundred times. With the actinic wavelength at 213 nm, the difference in energy between the pump and Stokes bands should be about 3500 cm$^{-1}$ in order to populate the v=3 level, and provide an absorption equal 195 nm photon. This energy difference would cause the v=3 level to be populated. A similar argument can be made for fluorescent SISC applications in the blue, green or red region of the spectrum, where absorption edges may extend for 50 nm.

The operation of PEARC bares similarity to the operation of phase shifting masks used in semiconductor photolithography. However, because two different wavelengths interfere to produce interference two separate masks, are used to synthesize the image with hyper-resolution. An example of a dual mask micro-lithography system is shown in FIG. 8. The interfering Stokes laser beam 140 from the second Stokes laser 110 is directed through Stokes phase mask 810, while the beams 132, 136, 138 (and optionally 142) are directed through actinic mask 820. The polarization, phase and intensity control modulators in the beam paths of laser beams 132, 136, 138, 140 have been omitted from FIG. 8 for sake of clarity; however, their configurations would be similar those shown in FIG. 1 and FIG. 2. The mask 820 (FIG. 8) will create the surround induced resolution narrowing as the π-wave plate which produces the annular beam in the point scanning microscope. The two-mask embodiment is useful for high definition hyper-resolution PEARC patterning of photoresists. The printed feature pitch cannot be higher than the spatial frequency transfer function of the reduction scanner lens, which is defined by the lens NA and the exposure wavelengths. Therefore, to print a pitch greater than the objective's resolution, the wafer must be micro-stepped a defined fraction of the transfer function resolution to produce multiple exposures within a single photoresist laser. This is called a double or multiple step exposure. A key advantage of this approach is that the photoresist need not be developed between micro stepped exposures. The actinic wavelength may be in the deep UV, but of a wavelength longer than the long wavelength absorption edge of the photoresist material. The maximum pitch is determined by the pump and Stokes wavelengths, which will likely be longer than the actinic wavelength. Feature critical dimension size in this system will likely be less than 10 nm.

Figure 9:
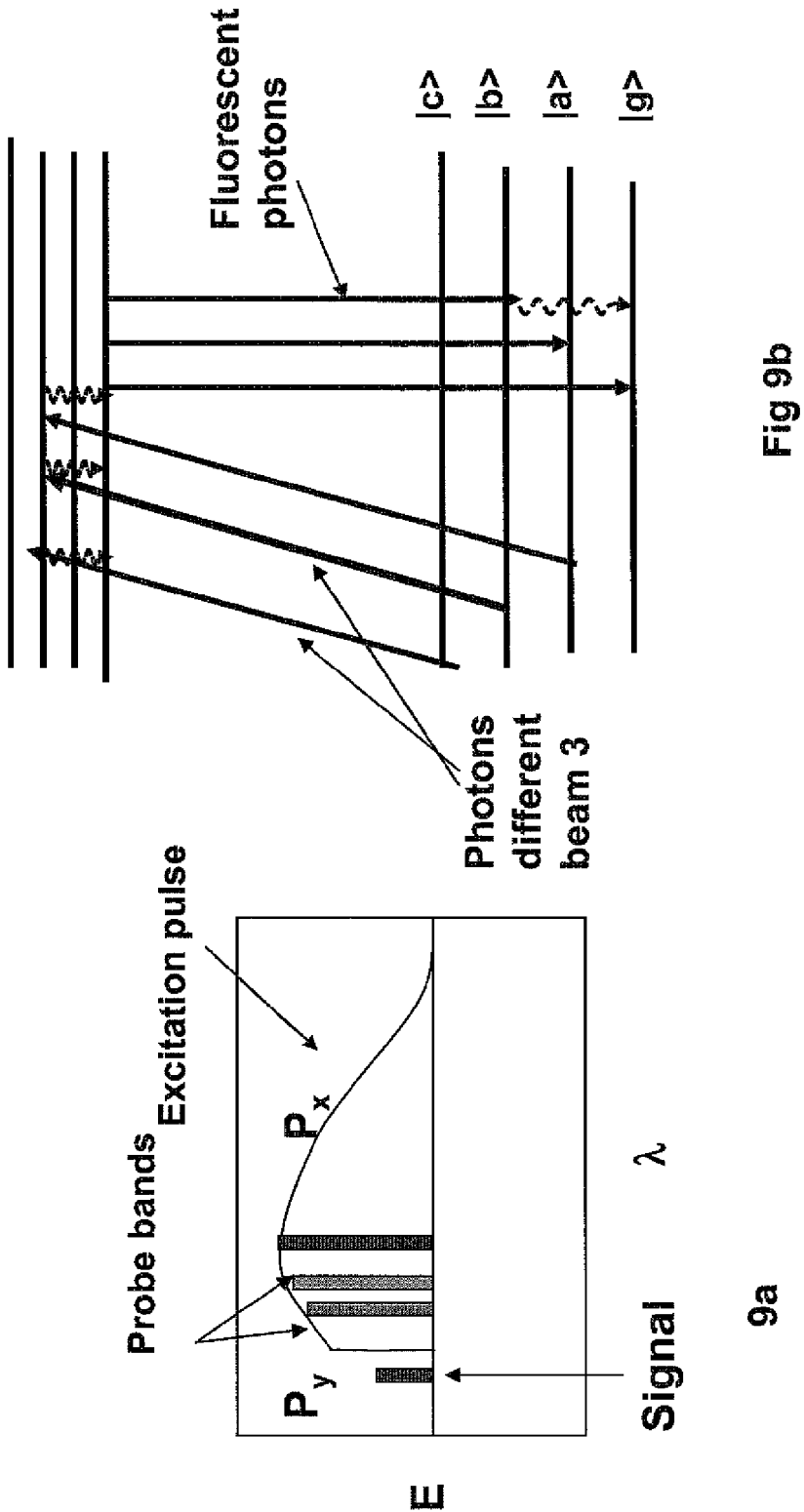
FIG. 9 shows incoherent addition of various wavelength actinic photons to produce fluorescence-encoded Raman spectroscopy.

The FEARE system can be used to encode Raman signals into highly efficient fluorescence emission. This can increase the efficiency of Raman detection by orders of magnitude. Multiple Raman signals can be encoded in one fluorescent emission line as illustrated in FIG. 9. This is achieved when a broad band femtosecond laser is used as the Stokes laser 108 to populate several vibrational levels. A different broad band laser can then be used as the actinic laser 140 to cause electronic excitation from multiple lines into a single fluorescent emission band. The actinic lines may be selected using a liquid crystal modulator to select various wavelengths after spectral dispersion with a system similar to the system show in FIG. 2. In this case, the unique identity of each line is lost. The identity of each line can be recovered if multiple different combinations of actinic lines are redundantly encoded as in Hadamard Transform Spectroscopy. Hadamard spectroscopy demonstrates significant enhanced signal to noise ratio over scanning spectral acquisition because of the multiple sampling of each wavelength.

FIG. 10 shows the Point-Spread-Functions (PSF) of a 1.3 NA system operating at 220 nm for the Stokes wavelength. This might be used for 157 nm or 193 nm photoresist. This calculation is indicative of the resolutions that are achievable with FEARE/PEARC and hyper-resolution CARS systems. These calculations assume that a confocal Point-Spread-Function PSF of the central excitation is a Gaussian $h_{cf}(x) = \exp(-4\ln2(x)^2/d_{cf}^2)$, wherein $d_{cf} = \lambda_{sc}/(2NA)$. The variable x is the distance for the center of focal spot, $\lambda_{sc}$ is the wavelength of the central Stokes beam and $d_{cf}$ is the Full Width at Half Maximum (FWHM) of the confocal microscope in terms of the microscope NA. The Stokes annular intensity is modeled as a parabola with a steepness ρ. The intensity of the parabola is defined $I(x) = 4I_{ASTIM} p^2 x^2$, wherein $I_{ASTIM}$ is the maximum intensity of the annulus. In FIG. 10, the intensity is normalized to the peak intensity of the central Stokes beam. This intensity of the central Stokes beam produces fluorescent emission at its center. The curve 1001 shows the PSF for the microscope with no annular illumination. Curves 1002, 1003, and 1004 show the PSF when the annular intensity is 1, 2, and 8 times that of the central Stokes illumination, respectively. The PSF half-width shrinks to about finm for curve 1004.

FEARE/PEARC imaging may be used to image many various types of molecules and organelles at better than 10 nm resolution. Raman emission bands are defining for proteins, nucleic acids in RNA and DNA and for lipids. Also small drug molecules may be imaged with precise Raman scattering signals. The ultra-high spatial resolution imaging disclosed in this application may therefore enable imaging of DNA structures, ribosomes, actin filaments, and physiological concentrations of unlabelled small molecule drugs and the spatial relationship of these molecules without external labels. The structure and position of neurotransmitter enclosed vesicles and the base sequence motifs of nucleic acids may be explored with very high resolution. A resolution of better than 6 nm may be achieved with electron-resonance FEARE at 260-340 nm and water immersion UV imaging. That is close to the length of one turn of a double helix of DNA and about 25 base pairs. Thus the FEARE microscope would be a replacement for electron microscopic imaging with similar resolution and no requirement for denaturing stains and with simultaneous molecular identity resolution.

Another application may be high-resolution mapping of tissue from ultra-thin sections to reveal, for example, the complete 3-dimensional connectivity of unstained or stained sections in the brain. The entire connection network of the brain is called the connectosome. Single molecule detection in Raman spectroscopy has been enabled with Surface Plasmon Enhancement on molecules attached to certain metal substrates. Surface Plasmon Resonance (SPR) enhanced Raman scattering has been shown to enhance the efficiency of Raman Scattering by many orders of magnitude, and to approach that of fluorescent imaging. Surface Plasmon evanescent waves exponentially decay from the surface over a scale length of less than 100 nm. It is proposed to obtain very low concentration Raman or Resonant Raman, CARS, or weak fluorescent images in ultra thin tissue sections of <100 nm attached to surface plasmon layers using the Stokes Interference State Controlled (SISC) approach disclosed here. Single molecule SPR enabled CARS has been demonstrated. Therefore low concentration CARS-SISC imaging should also be possible. There are multiple embodiments of SPR microscopic systems that should work well with SISC techniques. SPR enhancement does not work well when the laser illumination is normal to a flat enhancement layer. Therefore surface plasmon enhancement layers may be nano-structured by deposition or lithographic approaches. In addition, it has recently been proposed that these layers may be fabricated as thin resonant cavity layers. For example, in fluorescence imaging, both the excitation wavelengths used in SISC, the pump and the actinic beams are angularly tuned to create surface plasmon waves on the metal surface. These create a focal Gaussian envelope around a sinusoidal interfering fields at about ⅓ the wavelength of the incident light. The interfering Stokes beams would still be used to create free space vibrational population inversions with a resolution defined by the free space field interference of the Stokes beams creating a small excitation within a 50 nm or smaller pump fringe. The signal can be acquired in the epi scattering direction or in a forward scattering direction through the thin metal layer with a Reverse Kretchmann (RK) configuration. This approach has the advantage of greatly enhancing the SISC signals and also creating even more localized signals. The RK configuration is also ideal for stimulated emission capture of forward scattered light in SPR enhanced stimulated Raman, CARS or fluorescent SISC. In thin sections UV or DUV SPR excitation may be used with full tissue penetration. In the UV these layers may be made of silver and in the DUV they may be fabricated with aluminum alloys. In thin sections DUV excitation of specific molecule may be used for resonance plasmon layers to provide very rapid chemical imaging at very low concentration levels. By tuning the vibrational resonant level mapping of multiple molecules may be preformed in a multiplexed manner. Processing speed is significantly enhanced and sample preparation is simplified compared to electron microscopy.

In Absorption Encoded Anti-Stokes Raman Emission (AE-ARE) imaging the pump and Stokes beams populate the spatially narrowed excited vibrational state. The actinic beam has lower energy than the molecular absorption. Therefore in un-stimulated molecules transmission will be high, while in stimulated molecules absorption will be enhanced. The difference in stimulated and unstipulated signals will create the scanned image. In thin sections and at high resolution, the small number of molecules in the target image spot will create well defined signals. In this mode, SIMP absorption imaging can replace the electron microscope when imaging molecules in biological and material applications.

The high resolution PEARC systems are expected to find applications in semiconductor lithographic imaging. It can be used in conjunction with interferometric imaging to pattern features of less than 10 nm in diameter. This may be a simpler approach to high resolution imaging than EUV lithographic patterning and sues normal reduction optics.

The enhanced emission efficiency of FEARE in conjunction with Hadamard spectroscopy may be an ideal system for the standoff detection of improvised explosive devices (IEDs).

FEARE enables metabolic optical imaging by providing Raman images of the ratio free and bound NADH/NAD+. For example, it has been shown that that micro-fluorometry of NADH in intact cells and tissues gives a continuous measurement of intracellular oxidation-reduction states in vivo. (This may be the optical equivalent of PET measurement of Glucose, but with sub-cellular resolution) In the past decade, quantitative NADH fluorescence measurements from tissues in a variety of different organs (including the breast and oral cavity) has shown significant differences between malignant and normal tissue type. Moreover, measuring the free vs. bound concentration of NADH (NADH/NAD+ratio) via two-photon Fluorescence Lifetime Microscopy (FLM) can be used to measure the metabolic state of normal and breast cancer cells and in brain tissue. The key advantage of using the lifetime components rather than the intensity of NADH is that the lifetime is independent of NADH concentration and does not need to be calibrated for variations in the throughput of the instrument. FEARE imaging can make these measurements directly by looking at the Raman signatures of free and bound NADH and FAD.

However, NADH imaging dose not give a clear interpretable image of tissue architecture, which historically has been the prime diagnostic in biopsies and determination of tissue pathology. This is precisely the information that FEARE imaging of intrinsic molecules including proteins and nucleic acids can provide, without using a stain. A clinician can see tissue margins and see cells with normal and abnormal metabolism.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed is:
1. A laser system for analyzing or exposing a sample to optical radiation, the system comprising:

a first light source producing monochromatic coherent pump light pulses having a duration in a picosecond range and a first wavelength;

a second light source producing monochromatic coherent Stokes light pulses having a duration in a picosecond range and a second wavelength energetically spaced from the first wavelength by a vibrational energy state of the sample and a Gaussian beam profile, wherein a difference of photon energy corresponding to the first wavelength and photon energy corresponding to the second wavelength populate the vibrational energy state of the sample;

a third light source being phase-locked to the second laser and producing monochromatic coherent interfering light pulses having a duration in a picosecond range and a third wavelength energetically spaced from the second wavelength by a second vibrational energy state of the sample;

a fourth light source producing coherent actinic light pulses having at least one fourth wavelength, wherein photon energy corresponding to the at least one fourth wavelength is substantially equal to an energy difference between the virtual energy state and a stable quantum state of the sample; and an optical assembly combining the light pulses from the first, second, third and fourth light sources into a pulsed overlapping light beam and focusing the overlapping light beam with a Gaussian beam profile for the pump, Stokes and actinic pulses and an annular beam profile for the interfering light pulses in a focal plane on or in the sample.

2. The laser system of claim 1, further comprising a wavelength-dispersive detector receiving radiation produced responsive to the overlapping light beam in the focal plane, said wavelength-dispersive detector configured for detection of spectrally resolved received radiation produced by interaction of the first, second, third and fourth wavelengths.

3. The laser system of claim 2, wherein the wavelength-dispersive detector comprises a grating spectrometer.

4. The laser system of claim 2, further comprising a fifth laser having a Gaussian beam profile and a wavelength suitable to produce stimulated emission from the stable quantum state of the sample.

5. The laser system of claim 1, further comprising a microscope stage arranged substantially at the focal plane and configured to receive the sample receiving the overlapping light beam.

6. The laser system of claim 5, wherein the microscope stage is configured for displacement parallel to the focal plane so as to produce a two-dimensional image of the sample by scanning the focal spot across the sample.

7. The laser system of claim 1, wherein the light pulses from the second light source and the light pulses from the third light source arrive in the focal plane with a 180° phase shift between temporal centers of the coherent light pulses from the second and third light source.

8. The laser system of claim 7, wherein the annular beam profile has an intensity of approximately zero at a location in the focal plane where the Gaussian beam from the first light source has maximum intensity.

9. The laser system of claim 1, wherein a temporal half-width of the pump light pulses is at least 30% smaller than a temporal half-width of the Stokes light pulses and a temporal half-width of the interfering light pulses.

10. The laser system of claim 9, wherein a temporal half-width of the pump light pulses is at most 12-15 times smaller than a temporal half-width of the Stokes light pulses and a temporal half-width of the interfering light pulses.

11. The laser system of claim 1, wherein the light beam from the interfering light source are split into two beams which are recombined in the focal plane to produce an interference pattern.

12. The laser system of claim 11, wherein the annular beam profile has an intensity of approximately zero at a location in the focal plane where the Gaussian beam from the first light source has maximum intensity.

13. The laser system of claim 1, wherein the annular beam profile at the third wavelength has a peak intensity in the focal plane that is approximately between two and ten times a peak intensity in the focal plane of the Gaussian beam at the second wavelength.

14. The laser system of claim 1, further comprising a first optical system arranged in a beam path of combined pump, Stokes and actinic light pulses, said first optical system constructed to image a first optical mask in the focal plane of the sample, and a second optical system arranged in a beam path of interfering light pulses, said second optical system constructed to image a second optical phase mask in the focal plane of the sample commensurate with the first optical mask, said second optical mask embodied as a phase mask.

15. The laser system of claim 14, wherein the sample is a photoresist and the first and second masks in combination produce an exposure pattern in the photoresist.

16. A method for stimulated fluorescence, absorption, fluorescence or Raman microscopy having resolution exceeding a diffraction limit, comprising the steps of:

producing monochromatic coherent pump light pulses having a duration in a picosecond range, a first wavelength and a Gaussian beam profile;

producing monochromatic coherent Stokes light pulses having a duration in a picosecond range, a second wavelength and a Gaussian beam profile, wherein the second wavelength is energetically spaced from the first wavelength by a vibrational energy state of the sample and a Gaussian beam profile, with a difference of photon energy corresponding to the first wavelength and photon energy corresponding to the second wavelength populate the vibrational energy state of the sample;

producing monochromatic coherent interfering light pulses being phase-locked to the Stokes light pulses and having a duration in a picosecond range and a third wavelength energetically spaced from the second wavelength by a second vibrational energy state of the sample and an annular beam profile;

producing monochromatic coherent actinic light pulses having at least one fourth wavelength and a Gaussian beam profile, wherein photon energy corresponding to the at least one fourth wavelength is substantially equal to an energy difference between the virtual energy state and a stable quantum state of the sample;

combining the pump, Stokes, interfering and actinic light pulses into a pulsed overlapping light beam and focusing the overlapping light beam in a focal plane; and spectrally-resolved detecting radiation responsive to the overlapping light beam in the focal plane.

17. A method for exposing photoresist with a spatial resolution exceeding a diffraction limit, comprising the steps of:

producing monochromatic coherent pump light pulses having a duration in a picosecond range and a first wavelength;

producing monochromatic coherent Stokes light pulses having a duration in a picosecond range and a second wavelength, wherein the second wavelength is energetically spaced from the first wavelength by a vibrational energy state of the sample, with a difference of photon energy corresponding to the first wavelength and photon energy corresponding to the second wavelength populate the vibrational energy state of the sample;

producing monochromatic coherent interfering light pulses being phase-locked to the Stokes light pulses and having a duration in a picosecond range and a third wavelength energetically spaced from the second wavelength by a second vibrational energy state of the sample;

producing monochromatic coherent actinic light pulses having at least one fourth wavelength, wherein photon energy corresponding to the at least one fourth wavelength is substantially equal to an energy difference between the virtual energy state and a stable quantum state of the sample;

combining the pump, Stokes and actinic light pulses into a pulsed overlapping light beam having a Gaussian beam profile for the pump, Stokes and actinic pulses and an annular beam profile for the interfering light pulses, illuminating with the overlapping light beam a first optical projection mask, and projecting an image of the first optical projection mask on the photoresist; and illuminating a second optical projection mask embodied as a phase mask with the interfering laser beam and projecting an image of the second optical projection mask on the photoresist.

18. The method of claim 17, wherein the photoresist is disposed on a wafer to be patterned.

19. The method of claim 18, wherein the first optical projection mask is displaceable relative to the second optical projection mask.

* * * * *